(12) United States Patent
Lenz et al.

(10) Patent No.: US 7,722,661 B2
(45) Date of Patent: May 25, 2010

(54) STENT

(75) Inventors: Jason T. Lenz, Maplewood, MN (US); Daniel Gregorich, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 189 days.

(21) Appl. No.: 11/960,333

(22) Filed: Dec. 19, 2007

(65) Prior Publication Data

US 2009/0163991 A1    Jun. 25, 2009

(51) Int. Cl.
*A61F 2/06* (2006.01)
*A61F 2/90* (2006.01)

(52) U.S. Cl. .................. 623/1.15; 623/1.1; 623/1.17; 623/1.2; 623/1.39

(58) Field of Classification Search ............... 623/1.39, 623/1.42, 1.1–1.22
See application file for complete search history.

(56) References Cited

U.S. PATENT DOCUMENTS

| | | | |
|---|---|---|---|
| 4,733,665 A | 3/1988 | Palmaz |
| 5,133,732 A | 7/1992 | Wiktor |
| 5,139,480 A | 8/1992 | Hickle et al. |
| 5,183,085 A | 2/1993 | Timmermans |
| 5,195,984 A | 3/1993 | Schatz |
| 5,242,399 A | 9/1993 | Lau et al. |
| 5,314,444 A | 5/1994 | Gianturco |
| 5,421,955 A | 6/1995 | Lau et al. |
| 5,425,739 A | 6/1995 | Jessen |
| 5,441,515 A | 8/1995 | Khosravi et al. |
| 5,443,477 A | 8/1995 | Marin et al. |
| 5,494,029 A | 2/1996 | Lane et al. |
| 5,496,277 A | 3/1996 | Termin et al. |
| 5,507,767 A | 4/1996 | Maeda et al. |
| 5,507,771 A | 4/1996 | Gianturco |
| 5,514,154 A | 5/1996 | Lau et al. |
| 5,522,882 A | 6/1996 | Gaterud et al. |
| 5,531,741 A | 7/1996 | Barbacci |
| 5,549,662 A | 8/1996 | Fordenbacher |
| 5,603,721 A | 2/1997 | Lau et al. |
| 5,741,293 A | 4/1998 | Wijay |
| 5,797,898 A | 8/1998 | Santini et al. |
| 5,824,037 A | 10/1998 | Fogarty |
| 5,824,040 A | 10/1998 | Cox |
| 5,891,108 A | 4/1999 | Leone et al. |
| 5,902,266 A | 5/1999 | Leone et al. |
| 5,902,499 A | 5/1999 | Richerzhagen |
| 5,925,061 A | 7/1999 | Ogi et al. |
| 5,972,027 A | 10/1999 | Johnson |

(Continued)

FOREIGN PATENT DOCUMENTS

DE    19916086    10/1999

(Continued)

*Primary Examiner*—Thomas J Sweet
*Assistant Examiner*—Yashita Sharma
(74) *Attorney, Agent, or Firm*—Vidas, Arrett & Steinkraus

(57) ABSTRACT

A stent with strut bands and connectors, wherein the strut bands have long and short struts with a junction positioned between the short struts. Each junction defines a reservoir, wherein the reservoirs of a strut band are substantially circumferentially aligned. The connectors each have arms, wherein each arm includes an opposing U-shaped link. The opposing links have a shared portion disposed between a peak on one strut band and a longitudinally adjacent trough of an adjacent strut band.

14 Claims, 3 Drawing Sheets

U.S. PATENT DOCUMENTS

| | | | |
|---|---|---|---|
| 6,071,305 A | 6/2000 | Brown et al. |
| 6,132,461 A | 10/2000 | Thompson |
| 6,156,062 A | 12/2000 | McGuinness |
| 6,206,915 B1 | 3/2001 | Fagan et al. |
| 6,231,598 B1 * | 5/2001 | Berry et al. | 623/1.15 |
| 6,241,762 B1 | 6/2001 | Shanley |
| 6,254,632 B1 | 7/2001 | Wu et al. |
| 6,273,908 B1 | 8/2001 | Ndondo-Lay |
| 6,273,913 B1 | 8/2001 | Wright et al. |
| 6,355,055 B1 | 3/2002 | Waksman et al. |
| 6,379,381 B1 | 4/2002 | Hossainy et al. |
| 6,379,382 B1 | 4/2002 | Yan |
| 6,387,124 B1 | 5/2002 | Buscemi et al. |
| 6,395,326 B1 | 5/2002 | Castro et al. |
| 6,506,437 B1 | 1/2003 | Harish et al. |
| 6,551,838 B2 | 4/2003 | Santini et al. |
| 6,558,733 B1 | 5/2003 | Hossainy et al. |
| 6,562,065 B1 | 5/2003 | Shanley |
| 6,635,082 B1 | 10/2003 | Hossainy et al. |
| 6,656,162 B2 | 12/2003 | Santini et al. |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,699,281 B2 | 3/2004 | Vallana et al. |
| 6,709,379 B1 | 3/2004 | Brandau |
| 6,783,543 B2 | 8/2004 | Jang |
| 6,790,227 B2 * | 9/2004 | Burgermeister | 623/1.15 |
| 6,849,089 B2 | 2/2005 | Stoll |
| 7,135,039 B2 | 11/2006 | DeScheerder et al. |
| 2002/0038146 A1 | 3/2002 | Haryy |
| 2003/0125803 A1 | 7/2003 | Vallana et al. |
| 2004/0024449 A1 | 2/2004 | Boyle |
| 2004/0034337 A1 | 2/2004 | Boulais et al. |
| 2004/0044401 A1 * | 3/2004 | Bales et al. | 623/1.22 |
| 2004/0204750 A1 | 10/2004 | Dinh |
| 2004/0254635 A1 | 12/2004 | Shanley et al. |
| 2006/0224234 A1 | 10/2006 | Jayaraman |

FOREIGN PATENT DOCUMENTS

| | | |
|---|---|---|
| EP | 0623354 | 11/1994 |
| EP | 0931520 | 7/1999 |
| EP | 0950386 | 10/1999 |
| EP | 0747069 | 9/2002 |
| WO | 98/23228 | 6/1998 |
| WO | 98/51238 | 11/1998 |
| WO | 99/16386 | 4/1999 |
| WO | 9956907 | 11/1999 |
| WO | 03037223 A1 | 5/2003 |
| WO | 03055414 A1 | 7/2003 |

* cited by examiner

STENT

CROSS-REFERENCE TO RELATED APPLICATIONS

Not Applicable

STATEMENT REGARDING FEDERALLY SPONSORED RESEARCH

Not Applicable

FIELD OF THE INVENTION

This invention relates to an endoprosthesis device for implantation within a body vessel, typically a blood vessel. More specifically, it relates to a tubular expandable stent having improved structural aspects as well as improved drug retention/delivery capabilities.

BACKGROUND OF THE INVENTION

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to support body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled, and/or from one or more interwoven wires or braids.

Known construction materials for use in stents include polymers, organic fabrics, and biocompatible metals. Metals and/or alloys of such metals that have been used in the construction of stents and/or their components include but are not limited to: stainless steel, gold, silver, tantalum, titanium, chromium, cobalt and shape memory alloys such as Nitinol.

In an effort to combat vessel restenosis, as well as other medical conditions, stents have been employed to delivery a variety of therapeutic agents directly to the site of stent deployment. Some stents employ a variety of structural features, such as slots, grooves, holes, chambers, etc, to act as reservoirs for a therapeutic agent and/or other substances.

There remains a need for drug delivery stents that have improved structural performance characteristics, such as improved flexibility, structural integrity, compression resistance, etc. There also remains a need to provide such stents with a more desirable drug delivery profile.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 172. The abstract is not intended to be used for interpreting the scope of the claims.

BRIEF SUMMARY OF THE INVENTION

Embodiments of the present invention are directed to stent structures, which when used for the delivery of therapeutic agents such as drugs, provide improved drug delivery characteristics. The unique arrangement and configuration of drug delivery reservoirs throughout the stent structure provide improved drug delivery characteristics without compromise to the stent's performance characteristics.

Embodiments of the present invention include stents, which have improved flexibility, but also sufficient structural strength to permit the stents to traverse the tortuous confines of mammalian anatomy. In some embodiments the stent of the present invention are provided with strut bands of long and short struts, wherein pairs of short struts are connected to one another at junctions. The junctions provide a circumferential offset within the strut band.

In some embodiments the stents are provided with connectors between the strut bands, which have opposingly oriented U-shaped links, wherein each link extends from a junction of adjacent strut bands.

The combination of the structural features provided in the stents of the present invention provide a structurally improved, highly flexible stent.

An additional goal of the present invention however, is to provide stents with improved drug delivery characteristics as well. This goal is achieved by providing stents with drug delivery reservoirs that are positioned in and defined by the strut band junctions, as well as the connectors, and in some cases the struts as well. In some embodiments at least some of the reservoirs are provided in circumferentially aligned columns about the stent.

Reservoirs can be any type of surface feature suitable for containing a defined amount of therapeutic agent(s) such as a drug or drug/polymer matrix. In some embodiments one or more of the reservoirs extend only partially through the thickness of the stent with only a single opening on either the inner surface (luminal) or outer surface (abluminal) of the stent. In some embodiments, one or more of the reservoirs is a through-hole which extends entirely through the thickness of the stent body. Each reservoir can have a constant or varied cross-sectional area throughout its thicknesses. Each reservoir opening can have any of a variety of sizes or shapes.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
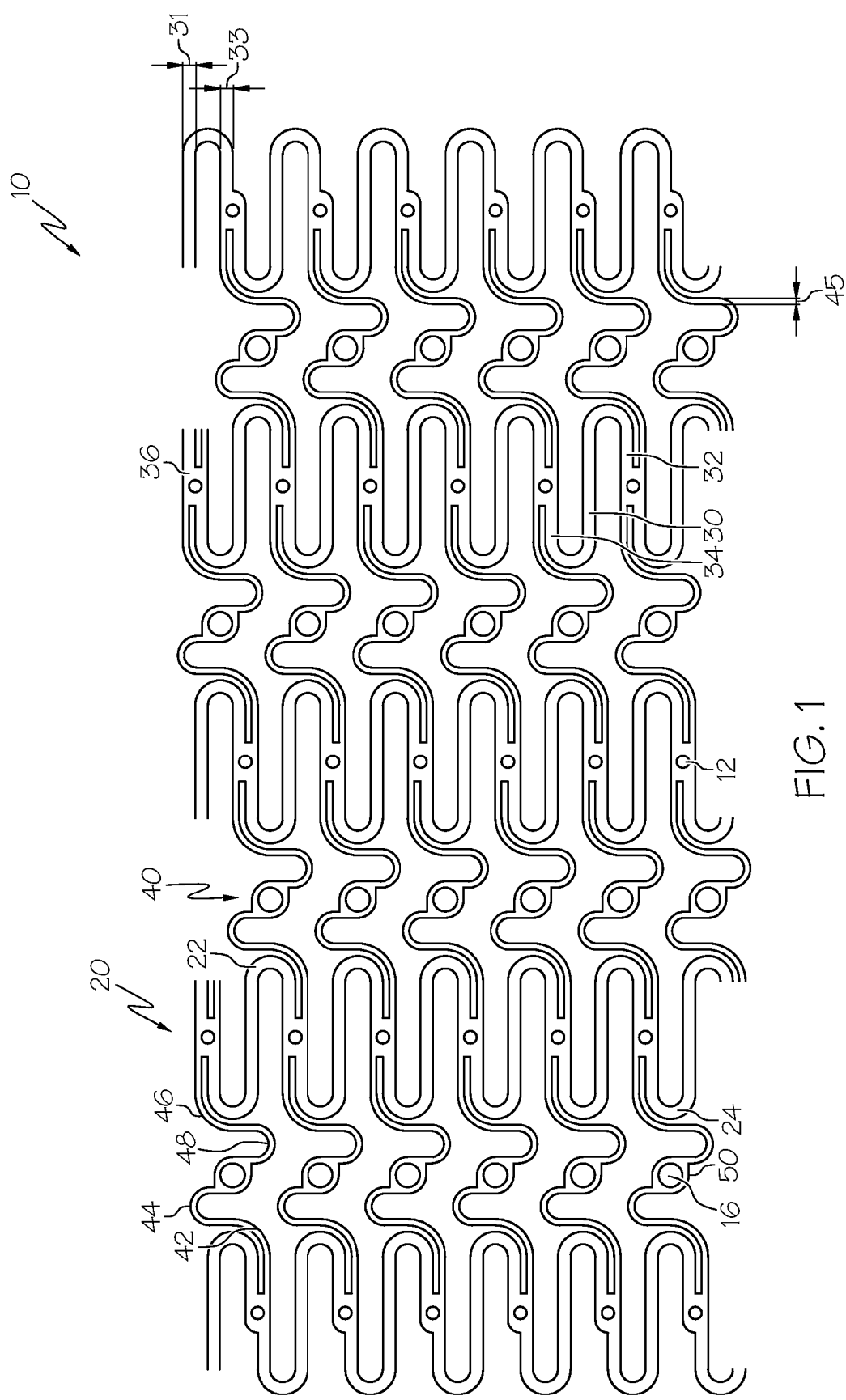
FIG. 1 shows a flat pattern view of an embodiment of the invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

At least one embodiment of the present invention is directed to a stent 10, an example of which is illustrated in FIG. 1. The structure of stent 10 is comprised of a plurality of strut bands 20 and connectors 40.

Each strut band 20 forms a closed path of alternating peaks 22 and troughs 24. Strut bands 20 that are adjacent one another are connected by at least one connector 40.

Each strut band 20 comprises a plurality of long struts 30, a plurality of first short struts 32 and second short struts 34, and a plurality of junctions 36. Each junction 36 is positioned between and connects a first short strut 32 and a second short strut 34. In the embodiments depicted in FIGS. 1-3, within each strut band 20 each first short strut 32 is longitudinally and circumferentially offset from each second short strut 34. Each long strut 30 is connected to a first short strut 32 at a peak 22 and to a second short strut 34 at a trough 24.

Figure 2:
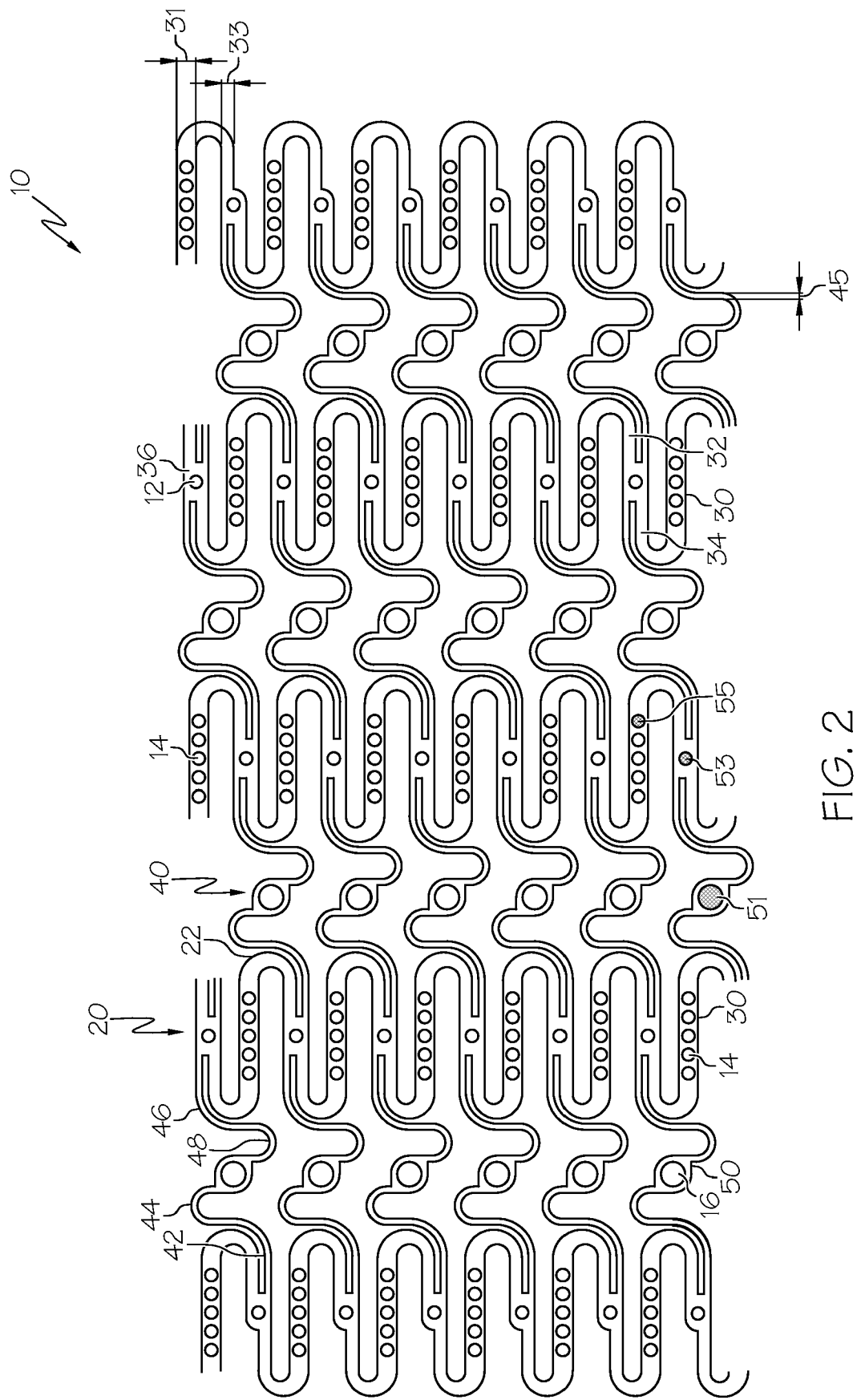
FIG. 2 shows a flat pattern view of an embodiment of the invention.
Figure 3:
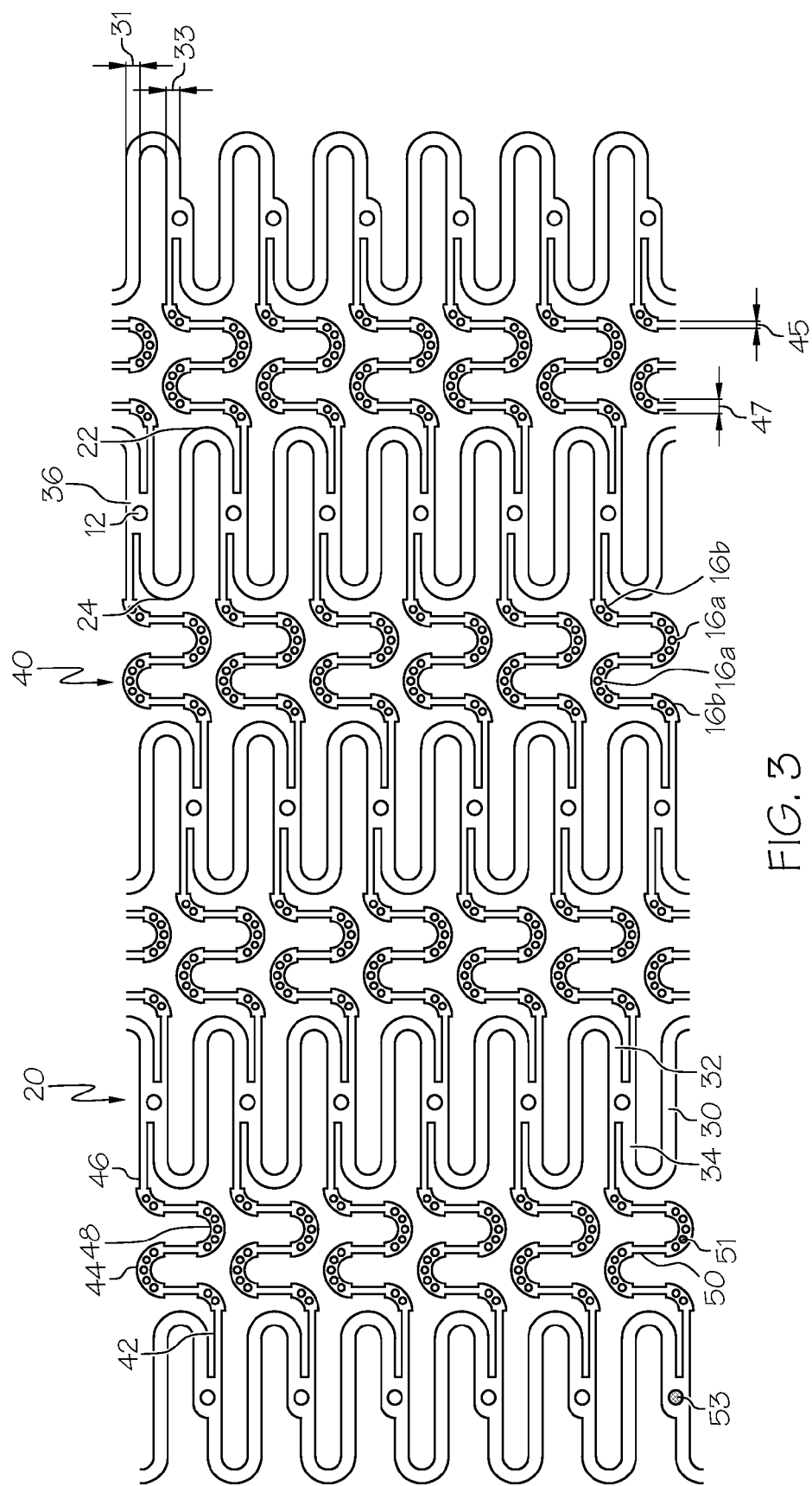
FIG. 3 shows a flat pattern view of an embodiment of the invention.

In the various embodiments shown in FIGS. 1-3 each junction 36 defines a single junction reservoir 12, wherein all of the junction reservoirs 12 of a given strut band 20 are substantially circumferentially aligned. In some embodiments however, a junction defines a plurality, such as 1, 2, 3, 4 or more junction reservoirs.

In some embodiments, the connectors 40 comprise a first arm 42 which extends from a junction 36 on one strut band 20 and a second arm 46 which extends from a junction 36 on an adjacent strut band 20. At least a portion of the first arm 42 comprises a first U-shaped link 44 and at least a portion of the second arm 46 comprises a second U-shaped link 48. Each first U-shaped link 44 opens in a first direction and each second U-shaped link 48 opens in a second direction substantially opposite the first direction. Though the specific orientation of the opening of the links can be varied and in any direction, in the embodiments shown in FIG. 1-3, each link 44 and 48 opens in a substantially circumferential direction or substantially perpendicular to a longitudinal axis of the stent 10.

At least a portion of the first U-shaped link 44 and at least a portion of the second U-shaped link 48 have a shared portion 50. The shared portion 50 of each connector 40 is disposed between one of the peaks 22 on one strut band 20 and a longitudinally adjacent trough 24 of an adjacent strut band 20. In embodiments where the stent 10 includes a plurality of connectors 40 between adjacent strut bands 20, the shared portions 50 between any two strut bands 20 are substantially circumferentially aligned.

If desired the strut bands 20 or a single continuous can be angled relative to a longitudinal axis of the stent to provide the band(s) with a helical or helical-like configuration. In such an embodiment the shared portions 50 of connectors 40 between a given pair of strut bands 40 can likewise be slanted or angled relative to the longitudinal axis.

In the embodiment depicted in FIG. 2 each long strut 30 defines at least one strut reservoir 14. In some embodiments, one or more of the long struts 30 define a plurality of strut reservoirs 14. The number of strut reservoirs 14 on a given long strut 30 can be varied from one to about twelve, depending on the length of the long strut 30. In some embodiments the number of strut reservoirs 14 is between at least three to nine. In the embodiment depicted in FIG. 2, in each long strut 30 one of the strut reservoirs 14 is in substantial circumferential alignment with the junction reservoirs 12 of a given strut band 20. Where there is a plurality of strut reservoirs 14 on a long strut 30, preferably the additional reservoirs 14 are spaced equidistantly from one another and are distributed evenly on either side of the central reservoir in circumferential alignment with the junction reservoirs 12.

The various components of a stent (struts, connectors, reservoirs, etc.) can have a variety of physical characteristics, such as length, width, thickness, etc, of which each can also be varied. In the embodiments depicted in FIG. 2 however, each long strut 30 has a long strut width, 31 and each first and second short strut 32/34 has a short strut width 33. The long strut width 31 is greater than the short strut width 33. Alternatively, in the embodiment shown in FIGS. 1 & 3 long strut width 31 is substantially the same as the short strut width 33.

In some embodiments, such as those shown in FIGS. 1 and 2, each arm 42 and 46 of the connectors 40 have an arm width 45. The arm width is less than either the long strut width 31 or the short strut width 33. In at least one embodiment, such as is depicted in FIG. 3, the width 45 of the arms 42 and 46 can vary along their lengths, particularly if the presence of connector reservoirs 16 necessitate a greater width region 47 in order to accommodate the desired cross-sectional area of the reservoirs 16.

In some embodiments, such as for example those depicted in FIGS. 1-2 the shared portion 50 of each connector 40 defines a single connector reservoir 16. As can be seen in the illustrations, the cross-sectional area 51 of a given connector reservoir 16 is greater than the cross-sectional area 53 of junction reservoir 12 or the cross-sectional area 55 of a strut reservoir 14 (areas 51, 53, and 55 are depicted shaded).

In some embodiments such as in the stent 10 depicted in FIG. 3, at least a portion of the first U-shaped link 44, adjacent to the shared portion 50, defines at least one connector reservoir 16 and at least a portion of the second U-shaped link 48, adjacent to the shared portion 50, defines at least one connector reservoir 16. In the embodiment shown, the area 51 of each connector reservoir is less than or substantially equal to the area 53 of each junction reservoir 12.

In the embodiment depicted in FIG. 3 the first U-shaped link 44 and the second U-shaped link 48 each define a plurality of first connector reservoirs 16a. A region of the first arm 42 adjacent the first U-shaped link 44 and a region of the second arm 46 adjacent the second U-shaped link 48 each define a second plurality of connector reservoirs 16b. The first plurality 16a is greater than the second plurality 16b.

The particular configuration and arrangement of the connector reservoirs 16 is not limited to only those configurations/patterns shown in FIGS. 1-3. The distribution, size, shape and configuration of the connector reservoirs (as well as the junction reservoirs and strut reservoirs) can be modified, in order to provide desired distribution/elution characteristics of one or more drugs or other therapeutic agents.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The stent 10 shown and described herein may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include, but are not limited to: platinum-iridium alloys, cobalt-chromium alloys, including Elgiloy and Phynox, MP35N alloy and nickel-titanium alloys, for example, Nitinol.

The stent 10 may be made of shape memory materials such as superelastic Nitinol or spring steel, or may be made of materials which are plastically deformable. In the case of shape memory materials, the stent may be provided with a memorized shape and then deformed to a reduced diameter shape. The stent 10 may restore itself to its memorized shape upon being heated to a transition temperature and having any restraints removed therefrom.

The stent 10 may be manufactures by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the stent 10 disclosed herein.

In some embodiments the stent 10, or its delivery system, may include one or more areas, bands, coatings, members, etc. that is (are) detectable by imaging modalities such as X-Ray, MRI, ultrasound, etc. In some embodiments at least a portion of the stent is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising:
   a plurality of strut bands, each strut band forming a closed path of alternating peaks and troughs, wherein strut bands adjacent to one another are connected by a plurality of connectors,
   each strut band comprising a plurality of long struts, a plurality of short struts, and a plurality of junctions, each junction being positioned between and connecting a first short strut and a second short strut, each long strut being connected to a first short strut at a peak and each long strut being connected to a second short strut at a trough,
   each junction defining only a single junction reservoir, each junction reservoir having a junction reservoir area, all of the junction reservoirs of a strut band being circumferentially aligned,
   each connector comprising a first arm which extends from a junction on one strut band, and a second arm which extends from a junction on an adjacent strut band, at least a portion of the first arm comprising a first U-shaped link and at least a portion of the second arm comprising a second U-shaped link, each first U-shaped link opening in a first direction and each second U-shaped link opening in a second direction substantially opposite the first direction, at least a portion of the first U-shaped link and at least a portion of the second U-shaped link having a shared portion, the shared portion disposed between one of the peaks on one strut band and a longitudinally adjacent trough of an adjacent strut band, the shared portion defining a single connector reservoir, each connector reservoir having a connector reservoir area, the connector reservoir area being greater than the junction reservoir area.

2. The stent of claim 1 wherein each first short strut is longitudinally and circumferentially offset from each second short strut.

3. The stent of claim 1 wherein each long strut defines at least one strut reservoir.

4. The stent of claim 3 wherein in each strut band, the at least one strut reservoir is in substantial circumferential alignment with the junction reservoirs.

5. The stent of claim 3 wherein each long strut defines a plurality of strut reservoirs, wherein at least one of the plurality of strut reservoirs is substantially circumferentially aligned with the junction reservoirs.

6. The stent of claim 5, wherein each of the plurality of strut reservoirs are spaced substantially equidistantly from one another along a length of the long strut.

7. The stent of claim 6 wherein each long strut defines between at least three strut reservoirs to nine strut reservoirs.

8. The stent of claim 1 wherein each long strut has a long strut width, and each short strut has a short strut width, the long strut width being greater than the short strut width.

9. The stent of claim 1 wherein each long strut has a long strut width, each short strut has a short strut width, and each arm has an arm width, the arm width being less than either the long strut width or the short strut width.

10. The stent of claim 1 wherein the shared portion of circumferentially adjacent connectors are substantially circumferentially aligned.

11. The stent of claim 1 wherein at least a portion of the first U-shaped link defines at least one connector reservoir and at least a portion of the second U-shaped link defines at least one connector reservoir.

12. The stent of claim 11 wherein each connector reservoir has a connector reservoir area, each junction reservoir having a junction reservoir area, the connector reservoir area being no greater than the junction reservoir area.

13. The stent of claim 12 wherein a region of the first U-shaped link adjacent to the shared portion defines a first connector reservoir, and a region of the second U-shaped link defines a second connector reservoir.

14. The stent of claim 13 wherein the first U-shaped link and the second U-shaped link each define a first plurality of connector reservoirs, and the region of the first arm adjacent the first U-shaped link and the region of the second arm adjacent the second U-shaped link each define a second plurality of connector reservoirs, wherein the first plurality is greater than the second plurality.

* * * * *